United States Patent
Harvey et al.

(12) 
(10) Patent No.: US 7,390,511 B2
(45) Date of Patent: Jun. 24, 2008

(54) COMPOSITIONS CONTAINING VITAMIN E AND SAW PALMETTO

(75) Inventors: Bryce M. Harvey, Pike Road, AL (US); V. Stan Mader, Fountain, CO (US)

(73) Assignee: ProEthic Pharmaceuticals, Inc., Montgomery, AL (US)

( * ) Notice: Subject to any disclaimer, the term of this patent is extended or adjusted under 35 U.S.C. 154(b) by 0 days.

(21) Appl. No.: 11/709,441

(22) Filed: Feb. 22, 2007

(65) Prior Publication Data

US 2007/0172528 A1     Jul. 26, 2007

Related U.S. Application Data

(63) Continuation of application No. 10/952,674, filed on Sep. 29, 2004, now Pat. No. 7,186,421.

(51) Int. Cl.
*A61K 33/04* (2006.01)
*A61K 33/30* (2006.01)
*A61K 31/335* (2006.01)

(52) U.S. Cl. .................. 424/727; 424/464; 424/702; 424/641; 424/643; 514/458

(58) Field of Classification Search ............... None
See application file for complete search history.

(56) References Cited

U.S. PATENT DOCUMENTS

| | | | |
|---|---|---|---|
| 6,511,675 B2 * | 1/2003 | Siddiqui et al. | 424/439 |
| 7,022,350 B2 * | 4/2006 | Harvey et al. | 424/727 |
| 7,186,421 B2 * | 3/2007 | Harvey et al. | 424/614 |
| 2005/0191368 A1 * | 9/2005 | Harvey et al. | 424/641 |
| 2005/0191369 A1 * | 9/2005 | Harvey | 424/641 |
| 2006/0121129 A1 * | 6/2006 | Harvey et al. | 424/641 |

\* cited by examiner

*Primary Examiner*—Susan Coe Hoffman
(74) *Attorney, Agent, or Firm*—Arnall Golden Gregory LLP; Clark G. Sullivan

(57) ABSTRACT

Mineral additives for preparing tablet compositions that comprise Vitamin E and optionally saw palmetto. The compositions are preferably formulated with a zinc compound and a selenium compound.

20 Claims, 1 Drawing Sheet

US 7,390,511 B2

COMPOSITIONS CONTAINING VITAMIN E AND SAW PALMETTO

RELATED APPLICATIONS

The present application is a continuation of, and claims priority to U.S. Ser. No. 10/952,674 filed Sep. 29, 2004 (granted Mar. 6, 2007 as U.S. Pat. No. 7,186,421). The contents of U.S. Ser. No. 10/952,674 are incorporated by reference.

FIELD OF THE INVENTION

The present invention is in the field of vitamin products, and relates particularly to tableted vitamin products that contain vitamin E and optionally saw palmetto, and methods of making such tablets.

DESCRIPTION OF RELATED ART

Vitamin E (e.g. tocopherols) and saw palmetto, and other plant-derived lipophilic vitamins, are notoriously difficult to formulate into solid dosage form because of their high oil content. Attempts at obtaining powders, tablets, or capsules of such oily materials have been largely unsuccessful, or have necessitated the inclusion of such compounds as hydrolyzed gelatin and/or complex formulation and processing techniques (e.g., spray drying or freeze drying) in order to obtain a solid powder which is capable of being easily tableted (see, for example, Japanese Patent Application JP 20247869A2). As a consequence, gel-caps are the preferred oral dosage form other than syrups and elixirs for vitamin products that contain large amounts of these vitamins. However, gel-caps suffer from their own disadvantages, because they are difficult to manufacture, and they can be especially difficult to formulate when one desires to incorporate other vitamins or minerals in the product that are not lipophilic.

Currently, a number of medicinal formulations contain herbal components or extracts from herbs. Many chemotherapeutic agents such as Taxol® and Vincristine are derivatives of botanical or herbal medicines that have successfully treated cancers. *Serenoa repens* (saw palmetto) is the most extensively studied phytotherapeutic agent for use in the treatment of lower urinary tract disorders and BPH.

A variety of herbal, dietary compositions have also been reported in the patent literature. For example, U.S. Pat. No. 5,665,393 to Chen, et al., describes an herbal composition for use in the treatment of prostate carcinoma containing Panax pseudo-ginseng, Isatis Indigotica Fort, Ganoderma lucidum Karst, Dendranthema morifolium Tzvel, Glycyrrhiza glabra, Scuttelaria baicalensis Georgi, Rabdosia rubescens, and Serenoa repens, all as alcohol extracts of the dried cut plants. While the patent states that the compositions can be administered orally or by suppository, it does not describe a formulation that could be formed into a tablet.

U.S. Pat. No. 6,261,607 to Newmark, et al, describes an herbal composition for use in the promotion of prostate health in men, prepared from saw palmetto, green tea, pumpkin seed oil, ginger, urtica root extracts, selenium, watermelon, and rosemary. The formulations are described as being suitable for oral administration, and contain approximately 320 mg of saw palmetto and 50 mcg of selenium in two capsules.

In U.S. Pat. No. 6,197,309, Wheeler discloses a neutraceutical composition for the prevention or improvement of prostatitis, and for relieving symptoms of prostatitis, wherein the composition includes therapeutically effective amounts of Vitamin C, Vitamin B6, Vitamin E, zinc, glycine, L-alanine, Glutamic acid, Saw palmetto, Pygeum extract, pumpkin seed, stinging nettle, Echinacea, garlic, Ginko biloba leaves, and selenium. Wheeler does not disclose a tablet formulation that can handle the large amounts of natural oils associated with tocopherols or Saw palmetto derived from natural sources.

Revel suggests compositions comprising lycopene, *Serenoa repens*, *Pygeum africanum*, and *Urtica dioica* (common stinging nettle) for the treatment of benign prostate hypertrophy and the prevention of prostate cancer in U.S Pat. No. 6,482,447. The components of the compositions are stated to have been specifically chosen and combined according to their biological activities, with *Pygeum africanum* extracts being included as a source of active lipid-soluble substances such as phystosterols, pentacyclic triterpenoids, and ferulic esters of fatty acid alcohols. Revel does not disclose a tablet formulation that contains large quantities of Saw palmetto or tocopherols.

Accordingly, there is a need for compositions and methods for formulating and delivering tocopherols, Saw palmetto, and other natural oil-containing vitamins, in tablet form.

SUMMARY OF THE INVENTION

It has unexpectedly been discovered that minerals such as zinc and selenium stabilize natural vitamin E and saw palmetto products, and that solid oral tablets can be manufactured having therapeutically meaningful quantities of vitamin E and saw palmetto by including zinc and selenium in the tableted formulation. In addition, precise ratios of zinc and/or selenium to vitamin E have been discovered that permit the manufacture of such tablets. Chelated forms of zinc and selenium have proven to be particularly advantageous in these applications.

Conditions for processing natural vitamin E and saw palmetto have also been discovered that permit the manufacture of solid oral tablets. In one of these embodiments, where the tablet contains both natural vitamin E and saw palmetto having high oil content, these two ingredients are separately formulated in dry admixtures with suitable mineral excipients such as zinc or selenium, and subsequently mixed into a dry intimate admixture before being compressed into a tablet. In another of these embodiments, strict manufacturing conditions are observed, and no more than 24 hours are allowed to pass after a dry flowable admixture is prepared from natural vitamin E or saw palmetto and natural vitamin E before compressing the admixture into tablets.

Formulations of natural vitamin E and natural vitamin E in combination with saw palmetto have also unexpectedly been discovered that contain:

a) about 150 IU of d-alpha tocopherol, about 25 mg. of d-gamma tocopherol, about 9 mg. of mixed tocopherols including both d-beta tocopherol and d-delta tocopherol, about 200 mcg. of selenium, about 5 mg. of lycopene complex, about 15 mg. of zinc, about 2 mg. of folic acid, about 500 mcg. of vitamin $B_{12}$ and about 25 mg. of vitamin $B_6$, or b) about 320 mg. of saw palmetto, about 75 IU of d-alpha tocopherol, about 12.5 mg. of d-gamma tocopherol, about 4.5 mg. of mixed tocopherols including both d-beta tocopherol and d-delta tocopherol, about 100 mcg of selenium, about 2.5 mg. of lycopene complex, about 7.5 mg. of zinc, about 1 mg. of folic acid, about 250 mg. of vitamin $B_{12}$ and about 12.5 mg. of vitamin $B_6$.

The foregoing formulations present numerous advantages including (1) their ability to be compressed into a tablet, (2) their ability to be formulated into an extended release tablet, and (3) their ability to be formulated into a mid-size tablet of minimal dimension and weight.

DETAILED DESCRIPTION OF THE INVENTION

I. Components of the Medicament

Saw Palmetto

Figure 1:
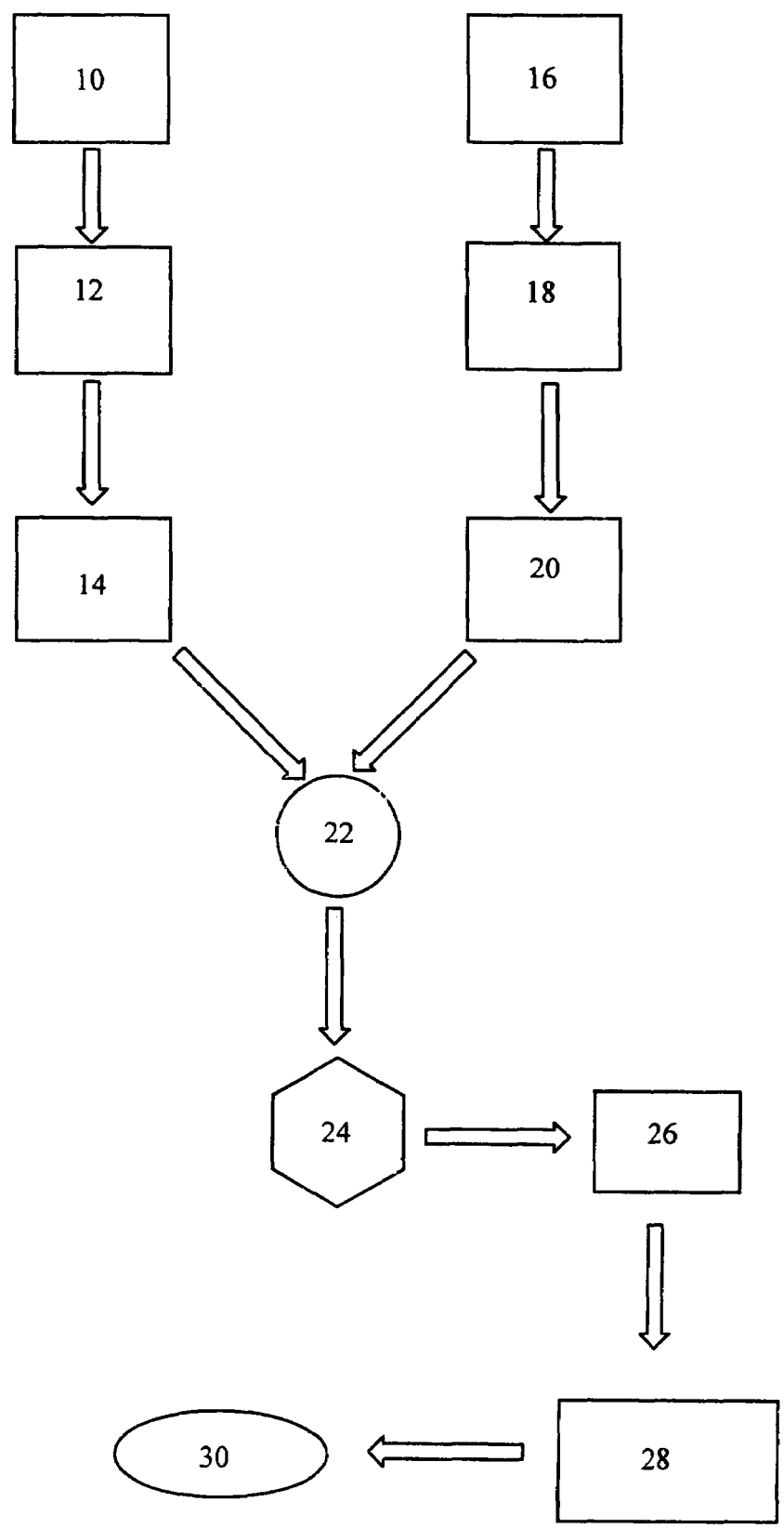
FIG. 1 shows a flowchart outlining the general process for formulating the compositions of the present invention.

Saw palmetto (a/k/a saw palmetto extract) reduces prostatic inflammation and swelling and improves uncomfortable urinary symptoms. Saw palmetto has been shown to inhibit 50% of the binding of DHT to receptor sites in the prostate thereby blocking the uptake of DHT into the nucleus of prostate cells. Saw palmetto also inhibits the action of testosterone 5 alpha-reductase thereby reducing the conversion of testosterone to DHT. The fatty acids, notably lauric and myristic acids, present in saw palmetto extract are mainly responsible for 5-alpha reductase inhibition, although the sterols and other ingredients in the saw palmetto are also known to confer beneficial effects. Saw palmetto can also improve urinary flow, reduce residual bladder urine volume, increase ease in commencing urination, decrease frequency of urination and decrease the need to empty the bladder at night. Saw palmetto as used herein is obtained from the natural product, *Serenoa repens*, or from saw palmetto berry's as an extract, using known methods for extracting the products (e.g., U.S. Pat. No. 6,599,540).

When used in the compositions of the present invention, saw palmetto is present in an amount ranging from about 45% to 86% by weight, preferably 60% to 80% by weight, and most preferably about 76% by weight and contains about 45% active saw palmetto ingredients. In a preferred embodiment, about 320 mg. of the saw palmetto of the present invention will consist of about 144 mg. of active ingredients (predominantly sterols and fatty acids). Optionally, and equally acceptable, the amount of saw palmetto present in the final formulation, when it is included, is from about 10 mg to about 1000 mg, more preferably from about 20 mg to about 1000 mg, and most preferably from about 20 mg to about 500 mg. In accordance with this, saw palmetto can be present in the final formulations of the compositions of the present invention which include this ingredient in an amount of about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 220 mg, about 240 mg, about 260 mg, about 280 mg, about 300 mg, about 320 mg, about 340 mg, about 360 mg, about 380 mg, about 400 mg, about 500 mg, about 600 mg, about 700 mg, about 800 mg, about 900 mg, about 1000 mg, and amounts in between any two of these given values.

In a preferred embodiment, the saw palmetto is present as a 30-60% extract from saw palmetto berries (preferably 40-50% and more preferably about 45%). Thus, for example, a preferred amount of 320 mg. of saw palmetto would contain about 144 mg. of fatty acids and sterols, which constitute the bulk of the active ingredients in the saw palmetto. In one embodiment the saw palmetto is not encapsulated an/or spray dried.

Vitamin E

Vitamin E is an antioxidant known to reduce prostate cancer and an immune stimulant that lowers cholesterol. In addition, the compound raises HDL, protects the nervous system and protects against cardiovascular disease. The vitamin regulates the way that cells lining the arteries proliferate and repair themselves thereby preventing the formation of blockages on the artery walls. There is an inverse association between plasma vitamin E levels and the incidence of heart disease.

The Vitamin E employed in the current invention is preferably derived 100% from natural sources (i.e. in enantiomerically pure mixtures). Several tocopherol isomers are preferably included in order to improve the therapeutic efficacy of the product. A large portion of the vitamin E is preferably present as d-alpha tocopherol, most preferably in the form of d-alpha tocopherol succinate because of the ease with which this tocopherol can be processed into tablet form and its concentrated biological activity. The d-alpha tocopherol is preferably present in an amount ranging from about 10% to 35% by weight, preferably 12% to 20% by weight, and most preferably about 15% by weight, of the entire formulation. The vitamin E is also preferably present as d-gamma tocopherol in an amount ranging from about 1% to about 9% by weight, preferably 2% to 7% by weight, and most preferably about 3% by weight, of the entire formulation. Mixed tocopherols (predominantly including d-beta tocopherol and d-delta tocopherol) are also preferably present in an amount ranging from about 0.5% to about 6% by weight, preferably 0.75% to 3% by weight, and most preferably about 1% by weight, of the entire formulation. The d-alpha and/or d-gamma tocopherol can be added to the formulation as part of the mixed tocopherols or as separate ingredients.

When the composition does not include an herb component such as saw palmetto, the d-alpha tocopherol or d-alpha tocopherol succinate is preferably present in an amount ranging from about 47% to 72% by weight, more preferably 52% to 65% by weight, and most preferably about 60% by weight, based upon the weight of the entire formulation. The d-gamma tocopherol is preferably present in an amount ranging from about 9% to about 21% by weight, more preferably 10% to 17% by weight, and most preferably about 12% by weight. The mixed tocopherols including d-beta tocopherol and d-delta tocopherol are preferably present in an amount ranging from about 1% to about 10% by weight, more preferably 2% to 7% by weight, and most preferably about 4% by weight.

Optionally, and equally acceptable, the amount of Vitamin E as d-alpha tocopherol or d-alpha tocopherol succinate present in the final formulation is from about 50 IU to about 500 IU, more preferably from about 50 IU to about 250 IU, and most preferably from about 50 IU to about 200 IU. As used herein, the unit "IU" stands for International Units and is used as a measurement of drugs and vitamins, in order to measure the quantity of a biologic (such as Vitamin E) that produces a particular biological effect agreed upon by an International Standard. In the case of Vitamin E (as d-alpha tocopherol succinate), there is about 1.47 IU/mg; thus, when there is 75 IU of d-alpha tocopherol in the final product composition, there is about 51 mg of d-alpha tocopherol present, and when there is 150 IU of d-alpha tocopherol in the final product composition, there is about 102 mg of d-alpha tocopherol present. In accordance with this, Vitamin E (as d-alpha tocopherol) can be present in the final formulations of the compositions of the present invention in an amount of about 25 IU, about 50 IU, about 75 IU, about 100 IU, about 125 IU, about 150 IU, about 200 IU, about 250 IU, and amounts in between any two of these given values.

Similarly, the amounts of Vitamin E as d-gamma tocopherol present in the final formulation composition can be from about 1 mg to about 100 mg, more preferably from about 5 mg to about 50 mg, and most preferably from about 10 mg to about 50 mg, as well as amounts in between any two of these given values. Mixed tocopherols predominantly as d-beta and d-delta tocopherol can be present in the final formulation composition in amounts from about 1 mg to about 50 mg, more preferably from about 1.5 mg to about 25 mg, and most preferably from about 2 mg to about 20 mg, as well as amounts in between any two of these given values.

The term "oily tocopherol," "non-hydrophilic tocopherol," and "lipophilic tocopherol" refer generally to the class of natural tocopherols that are difficult to process or formulate into solid tablets due to their excessive content of oils, also known as oleophilic tocopherols. By way of example and illustration, such tocopherols include d-gamma, d-beta, and d-delta tocopehrol, and exclude d-alpha tocopherol succinate. In like manner, the term "oily ingredients" include ingredients that are difficult to process or formulate into solid tablets due to their excessive content of oils, and can generally be assessed by comparison to oily and non-oily tocopherols. Unless otherwise indicated, the term oily tocopherol includes spray dried tocopherols. In one embodiment, the term "oily" tocopherol includes spray dried tocopherols. In another embodiment, the term "oily tocopherol excludes spray dried tocopherols.

Selenium

Selenium is a nonmetallic trace element recognized as a nutrient essential to human health. It has been surprisingly found that the inclusion of active minerals like selenium into formulations comprising high amounts of nutrients with natural oils enable the formulation of such nutrients into tablets by allowing for an absorbtion of some of these natural oils. This is especially true of the selenium chelate employed in the preferred formulations herein, because the chelate independently contributes to the processability of the tablets in addition to improving the bioavailability of the selenium mineral.

Selenium as used herein is preferably present as a selenium chelate, which includes but is not limited to selenium amino acid and protein chelates such as selenomethionine, selenocysteine, selenoaspartate, and selenoglycinate, selenium ascorbate, selenium citrate, selenium fumarate, selenium malate, selenium protein chelate, selenium succinate, selenium tartrate, selenium soy protein chelate, selenium rice chelate, selenium whey chelate, selenium cellulose chelate, and selenium yeast chelate. Preferably, the selenium is used as the selenium soy protein chelate. The chelate preferably is present as a 0.05-5%, 0.1-1.0%, or about a 0.2% selenium chelate.

Selenium (elemental) is present in the composition in an amount ranging from about 0.009% to 0.05% by weight, preferably 0.01% to 0.03% by weight, and most preferably about 0.02% by weight. When the composition does not include an herb component such as saw palmetto, selenium is present in the composition in an amount ranging from about 0.05% to 0.5% by weight, preferably 0.09% to 0.3% by weight, and most preferably about 0.1% by weight.

Additionally, and in accordance with the present invention, the selenium as an active mineral is present in a ratio from about 0.001 mg to about 0.01 mg per 1 mg of d-alpha tocopheryl succinate, and more preferably in a ratio from about 0.001 mg to about 0.002 mg per 1 mg of d-alpha tocopheryl succinate. Alternatively, and equally acceptable, the selenium as an active mineral can be present in a ratio from about 0.0002 to about 0.0004 mg per 1 mg of saw palmetto extract, and more preferably in a ratio of from about 0.0002 to about 0.0003 mg per 1 mg of saw palmetto extract.

Lycopene

Lycopene, a non-provitamin A carotenoid, accounts for the red color of fruits and vegetables such as tomatoes, pink grapefruit, the skin of red grapes, watermelon and red guavas and is the most efficient singlet-oxygen quencher among the natural carotenoids. Lycopene can be obtained by the isolation from tomatoes, tomato paste, tomato juice, or other tomato products; by supercritical $CO_2$ extraction (e.g., Baysal, T., et al., *J. Agricult. Food Chem.*, 48, pp. 5507-5511 (2000)); by saponification (U.S. Pat. No. 5,858,700); by biosynthetic methods; and synthetically using such industrial processes as those described by Meyer in European Patent No. EP 0 382 067, by Wegner, C., et al., in German Patent No. DE 100 09 459, and by Ernst in *Pure and Applied Chemistry*, Vol 74 (11), pp 2213-2226 (2002). Lycopene, as used herein refers to natural lycopene, synthetic lycopene, isomers of lycopene and mixtures of such isomers.

The lycopene is typically present as a lycopene complex (the term often given to lycopene isolated from natural products and containing several other compounds in association with the lycopene itself). Lycopene complex is present in the present compositions in an amount ranging from about 0.26% to 1% by weight, preferably 0.35% to 0.75% by weight, and most preferably about 0.6% by weight. When the composition does not include an herb component, lycopene complex is present in the composition in an amount ranging from about 0.5% to 5% by weight, preferably 1% to 4% by weight, and most preferably about 2% by weight. Optionally, and equally acceptable, the amount of lycopene complex present in the final formulation is from about 1 mg to about 10 mg, more preferably from about 2 mg to about 10 mg, and most preferably from about 2 mg to about 6 mg. In accordance with this, lycopene complex can be present in the final formulations of the compositions of the present invention in an amount of about 1 mg, about 1.5 mg, about 2 mg, about 2.5 mg, about 3 mg, about 3.5 mg, about 4 mg, about 4.5 mg, about 5 mg, about 5.5. mg, about 6 mg, about 6.5 mg, about 7 mg, about 7.5 mg, about 8 mg, about 8.5 mg, about 9 mg, about 9.5 mg, about 10 mg, and amounts in between any two of these given values.

Zinc

As used herein, zinc is preferably used as an organic or inorganic salt, including but not limited to zinc acetate, zinc amino acid complexes, zinc gluconate, zinc gluconate glycine, zinc citrate, zinc aspartate, zinc picolinate, zinc stearate, zinc sulfate, zinc undecylenate, or zinc chloride (e.g., Zincate™). Preferably, the zinc compound used within the present invention is a zinc/amino acid complex such as zinc gluconate, although any of the other known, similar zinc compounds are envisioned to be suitable for use in place of or in combination with zinc gluconate. The zinc is preferably present as a 5-20%, 10-15%, or about a 12% amino acid chelate. Most preferably, the zinc is present as a 12% zinc gluconate complex.

Zinc (elemental) is present in the composition in an amount ranging from about 1% to 21% by weight, preferably 1.2% to 5% by weight, and most preferably about 1.8% by weight. When the composition does not include an herb component, zinc is present in the composition in an amount ranging from about 2% to 11% by weight, preferably 4% to 9% by weight, and most preferably about 7% by weight.

Additionally, and in accordance with the present invention, the zinc as an active mineral (Zn) is present in a ratio from about 0.1 mg to about 0.5 mg per 1 mg of d-alpha tocopheryl succinate, and more preferably in a ratio from about 0.1 mg to about 0.2 mg per 1 mg of d-alpha tocopheryl succinate. Alternatively, and equally acceptable, the zinc as an active mineral can be present in a ratio from about 0.01 mg to about 0.1 mg per 1 mg of saw palmetto extract, and more preferably in a ratio of from about 0.01 mg to about 0.05 mg per 1 mg of saw palmetto extract. Most preferably, the amount of zinc as an active mineral can be present in a ratio of about 0.02 mg zinc per 1 mg of saw palmetto extract in the compositions of the present invention.

Folic Acid

Folic acid (structure below), also known as folate and folacin, is a water-soluble B vitamin that occurs naturally in food, such as liver, kidneys, mushrooms, spinach, yeast, green leaves, and grasses. Folic acid is known to be involved in the synthesis, repair and functioning of DNA, and a deficiency of folate may result in increased serum levels of homocysteine and damage to DNA that may lead to cancer. Folic acid suitable for use in the present invention can be isolated from natural products, can be obtained from commercial sources, or can be synthesized using methods such as those described by Gates, et al. (*Chem. Rev.*, 41, pp. 63-95 (1947)), Hkalifa, E., et al. (*Helv. Chim. Acta*, 56, pp. 242 (1976), and Al-Shammary, et al. (*Anal. Profiles Drug Subs.*, 19, pp. 221-259 (1990)). When used in the compositions of the present invention, folic acid is present in an amount ranging from about 0.1% to 2.5% by weight, preferably 0.15% to 1% by weight, and most preferably about 0.24% by weight. When the composition does not include an herb component, vitamin folic acid is present in an amount ranging from about 0.5% to 5% by weight, preferably 0.8% to 2% by weight, and most preferably about 1% by weight. Optionally, and equally acceptable, the amount of folic acid present in the final formulation is from about 1 mg to about 10 mg, more preferably from about 1 mg to about 8 mg, and most preferably from about 1 mg to about 5 mg. In accordance with this, folic acid can be present in the final formulations of the compositions of the present invention in an amount of about 1 mg, about 1.5 mg, about 2 mg, about 2.5 mg, about 3 mg, about 3.5 mg, about 4 mg, about 4.5 mg, about 5 mg, about 5.5. mg, about 6 mg, about 6.5 mg, about 7 mg, about 7.5 mg, about 8 mg, about 8.5 mg, about 9 mg, about 9.5 mg, about 10 mg, and amounts in between any two of these given values.

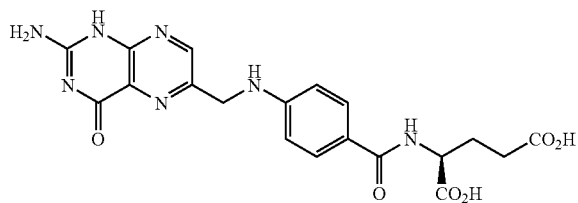

Cyanocobalamin (Vitamin $B_{12}$)

Vitamin $B_{12}$'S primary functions are in the formation of red blood cells and the maintenance of a healthy nervous system. Vitamin $B_{12}$ is necessary for the rapid synthesis of DNA during cell division. A deficiency of vitamin $B_{12}$ can increase serum levels of homocysteine and disrupt DNA production causing formation of megaloblasts and ultimately anemia. Cyanocobalamin (Vitamin $B_{12}$) as used herein can be obtained from commercial sources; isolated from natural sources or bacteria by known means, such as by biofermentation of *Streptomyces griseus*; by fermentation using *Pseudomonas denitrificans* (U.S. Pat. No. 3,018,225); or by organic synthesis means, such as that reported by R. B. Woodward (*Pure Appl. Chem.*, 33, p. 145 (1973)). When used in the compositions of the present invention, vitamin $B_{12}$ is present in an amount ranging from about 0.03% to 0.1% by weight, preferably 0.04% to 0.07% by weight, and most preferably about 0.06% by weight. When the composition does not include an herb component, vitamin $B_{12}$ is present in an amount ranging from about 0.1% to 1% by weight, preferably 0.2% to 0.7% by weight, and most preferably about 0.3% by weight. Optionally, and equally acceptable, the amount of cyanocobalamin (Vitamin $B_{12}$) present in the final formulation is from about 0.001 mg to about 100 mg, more preferably from about 0.1 mg (100 mcg) to about 50 mg, and most preferably from about 0.15 mg (150 mcg) to about 10 mg. In accordance with this, cyanocobalamin (Vitamin $B_{12}$) can be present in the final formulations of the compositions of the present invention in an amount of about 0.1 mg, about 0.15 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg, about 1 mg, about 2 mg, about 3 mg, about 4 mg, about 5 mg, about 10 mg, about 20 mg, about 30 mg, about 35 mg, about 40 mg, about 45 mg, about 50 mg, and amounts in between any two of these given values.

Vitamin $B_6$

Vitamin $B_6$ is a water-soluble vitamin that exists in three major chemical forms: pyridoxine (below), pyridoxal, and pyridoxamine, with pyridoxine hydrochloride being the predominant form. Vitamin $B_6$ is reported to boost immunity and prevent cancer in some instances. Vitamin $B_6$ also prevents blood clots that can block arteries. A deficiency of vitamin $B_6$ can increase serum levels of homocysteine and lead to hardened, narrowed arteries. Vitamin B6 (pyridoxine HCl) as used herein can be obtained from commercial sources, isolated from natural products such as cereals; by biofermentation of yeasts; via biosynthesis (Hiel, et al, *Science*, 169, p. 773 (1970)); and by known synthetic methods (e.g., Harris, et al., *J. Org. Chem.*, 27, p. 2705 (1962); Shono, T., et al., *Chem. Letters*, p. 1121 (1981); and in U.S. Pat. Nos. 2,904,551, 3,024,244, and 3,024,245 to Merck & Co).

When used in the compositions of the present invention, vitamin $B_6$ is present in an amount ranging from about 1% to 22% by weight, preferably 2% to 16% by weight, and most preferably about 3% by weight. When the composition does not include an herb component, vitamin $B_6$ is present in an amount ranging from about 4% to 27% by 5 weight, preferably 10% to 16% by weight, and most preferably about 12% by weight. Optionally, and equally acceptable, the amount of pyridoxine HCl present in the final formulation is from about 1 mg to about 100 mg, more preferably from about 1.5 mg to about 80 mg, and most preferably from about 1.5 mg to about 50 mg. In accordance with this, pyridoxine HCl can be present in the final formulations of the compositions of the present invention in an amount of about 1 mg, about 1.5 mg, about 2 mg, about 2.5 mg, about 3 mg, about 3.5 mg, about 4 mg, about 4.5 mg, about 5 mg, about 5.5. mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5 mg, about 15 mg, about 20 mg, about 25 mg, about 30 mg, about 35 mg, about 40 mg, about 45 mg, about 50 mg, and amounts in between any two of these given values.

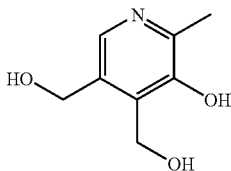

In a preferred embodiment of the invention, the active ingredients of the composition include about 124 mg of d-alpha tocopherol succinate, about 25 mg of d-gamma tocopherol, about 9 mg of mixed tocopherols including d-delta tocopherol and d-beta tocopherol, about 200 mcg of selenium, about 5 mg of lycopene complex, about 15 mg of zinc, about 2 mg of folic acid, about 500 mcg of cyanocobalamin and about 25 mg of pyridoxine HCl.

In another preferred embodiment of the invention, the active ingredients of the composition include about 320 mg. of saw palmetto, about 248 mg. of d-alpha tocopherol succinate, about 12.5 mg. of d-gamma tocopherol, about 4.5 mg. of mixed tocopherols including both d-beta tocopherol and d-delta tocopherol, about 100 mcg of selenium, about 2.5 mg. of lycopene complex, about 7.5 mg. of zinc, about 1 mg. of folic acid, about 250 mg. of vitamin $B_{12}$ and about 12.5 mg. of vitamin $B_6$ Excipients A number of excipients have been found to be useful for inclusion in the compositions of the present invention. Specifically useful are dicalcium phosphate, microcrystalline cellulose, starch, and silica.

Dicalcium phosphate can be included as a flow agent and compression aid in addition to aiding in oil absorption. Microcrystalline cellulose and cellulose can be included for use as disintegrants, binding agents, compressing agents, and for assisting in the absorbion of natural oils containing in saw palmetto and/or vitamin E's. Starch is included as a disintegrant and an oil absorber, while silica is included in the formulations of the present invention as a flow agent and an oil absorber. Magnesium stearate can be included in the formulations of the present invention as a surface lubricant, while polyvinylpyrrolidone can be included as both a binding agent and/or as a disintegrant.

In another preferred embodiment of the invention, the active ingredients of the composition include about 60% by weight of d-alpha tocopheryl succinate, about 12% by weight of d-gamma tocopherol, about 4% by weight of mixed tocopherols including d-delta tocopherol and d-beta tocopherol, about 0.1% by weight of selenium, about 2.4% by weight of lycopene complex, about 7.3% by weight of zinc, about 1% by weight of folic acid, about 0.24% by weight of cyanocobalamin and about 12% by weight of pyridoxine HCl.

In yet another preferred embodiment of the present invention, the active ingredients of the composition include about 52% to 65% by weight of d-alpha tocopheryl succinate, about 10% to 17% by weight of d-gamma tocopherol, about 2% to 7% by weight of mixed tocopherols including d-delta tocopherol and d-beta tocopherol, about 0.09% to 0.3% by weight of selenium, about 1% to 4% by weight of lycopene complex, about 4% to 9% by weight of zinc, about 0.8% to 2% by weight of folic acid, about 0.2% to 0.7% by weight of cyanocobalamin and about 10% to 16% by weight of pyridoxine HCl.

In a preferred embodiment of the invention including an herb component, the active ingredients of the composition include about 320 mg of saw palmetto, about 62 mg of d-alpha tocopheryl succinate, about 12.5 mg of d gamma tocopherol, about 4.5 mg of mixed tocopherols including d-delta tocopherol and d-beta tocopherol, about 100 mcg of selenium, about 2.5 mg of lycopene complex, about 7.5 mg of zinc, about 1 mg of folic acid, about 250 mcg of cyanocobalamin and about 12.5 mg of pyridoxine HCl.

In another preferred embodiment of the invention including saw palmetto, the active ingredients of the composition include about 76% by weight of saw palmetto, about 15% by weight of d-alpha tocopheryl succinate, about 3% by weight of d-gamma tocopherol, about 1% by weight of mixed tocopherols including d-delta tocopherol and d-beta tocopherol, about 0.02% by weight of selenium, about 0.6% by weight of lycopene complex, about 1.8% by weight of zinc, about 0.24% by weight of folic acid, about 0.06% by weight of cyanocobalamin and about 3% by weight of pyridoxine HCl.

In yet another preferred embodiment of the present invention including an herb component, the active ingredients of the composition include about 60% to 80% by weight of saw palmetto, about 12% to 20% by weight of d-alpha tocopheryl succinate, about 2% to 7% by weight of d-gamma tocopherol, about 0.75% to 3% by weight of mixed tocopherols including d-delta tocopherol and d-beta$_5$ tocopherol, about 0.01% to 0.03% by weight of selenium chelate, about 0.35% to 0.75% by weight of lycopene complex, about 1.2% to 5% by weight of zinc gluconate, about 0.15% to 1% by weight of folic acid, about 0.04% to 0.07% by weight of cyanocobalamin and about 2% to 16% by weight of pyridoxine HCl.

II. Methods of Making Composition

The invention provides various methods of making the formulations/compositions of the present invention. These methods are generally designed to solve the manufacturing problems associated with manufacturing tablets that have high contents of natural oils from the vitamin E and saw palmetto ingredients.

It has surprisingly been discovered that minerals such as zinc and selenium stabilize the natural oils in vitamin E and saw palmetto, and that such minerals overcome the historically difficult task of forming large amounts of these natural products into pharmaceutically acceptable tablets. In one embodiment, this surprising ability is measured by the ratio of zinc and/or selenium to the oily components in the formulation (i.e. the d-delta, d-beta, and d-gamma components of the vitamin E, and not the d-alpha component which is typically present in the less oily succinate form). The zinc and/or selenium is mixed in an intimate admixture with said vitamin E and/or saw palmetto in said tablets and in said admixture from which said tablets are formed. The term "intimate admixture" is a relative term, and means that there is sufficient contact between the minerals and oily components to effectively partition or absorb the oils from the mixture such that the mixture can be formed into a tablet by compression or molding techniques. The term excludes encapsulated ingredients.

It has surprisingly been found that the presence of zinc and/or selenium, in a formulation that contains large quantities of oily vitamin E components (such as the formulations of the present invention), will stabilize the vitamin E, and allow the formulation to be compressed into a sustained release tablet, when the weight ratio of zinc to oily vitamin E components equals or exceeds about 0.35, 0.40, or 0.45, preferably about 0.44, and the weight ratio of selenium to oily vitamin E components to selenium equals or exceeds about 0.0040, 0.0045, 0.0050, 0.0055, or 0.0060, preferably about 0.0059.

Remarkably, these ratios hold regardless of the presence of Saw palmetto in addition to the oily vitamin E components, as evidenced by the preferred formulations given in the examples hereof. Thus, in one embodiment the invention provides a method of making a tablet comprising natural oily tocopherols comprising: (a) admixing said tocopherols with zinc and selenium and optionally saw palmetto in a zinc:tocopherol weight ratio of greater than or equal to about 0.44 and a selenium:tocopherol weight ratio of greater than or equal to about 0.0059 to form an admixture, and (b) compressing said admixture into a tablet, wherein: (i) when present, said saw palmetto is present in a saw palmetto:tocopherol weight ratio of about 18.8, and (ii) preferably said tablet excludes other oily ingredients derived from natural sources.

The tablets of the present invention can be prepared according to the flow sheet shown in FIG. 1. As described therein, a first group of ingredients comprising saw palmetto, zinc gluconate, dicalcium phosphate, microcrystalline cellulose, starch, silica, and magnesium stearate are weighed out individually (10). These compounds are then combined and blended together (12) using an appropriate blending device (e.g., a Twin Shell Blender) as are known in the art, and then processed in an oscillator. The blended components are then Chilsonated through, for example, a Vector Roller Compactor (14).

Similarly, a second group of ingredients comprising Vitamin E succinate (d-alpha tocopheryl succinate), natural mixed tocopherols (incl. beta-, gamma-, and delta-tocopherols), cellulose, silica, magnesium stearate, chelated selenium, lycopene complex, folic acid, vitamin B12, vitamin B6, polyvinylpyrrolidone, dicalcium phosphate, and microcrystalline cellulose are weighed out individually (16). These compounds are then combined and blended together (18) using an appropriate blending device (e.g., a Twin Shell Blender) as known in the art, and processed further in an oscillator. The blended components are then Chilsonated through, for example, a Vector Roller Compactor (20).

The blended and chilsonated Group 1 and Group 2 ingredients are then combined (22) and blended in a blender (e.g., a Twin Shell Blender) for a period of time (e.g., for about 6 to about 10 minutes, preferably about 8 minutes). Excipients such as microcrystalline cellulose and silica are then added (24) and the mixture blended for a further period of time (e.g., from about 6 minutes to about 10 minutes, and preferably for about 8 minutes). Magnesium stearate is then added (26) and the final mixture blended for a final amount of time (e.g., 2 minutes). The final blended product is then compressed into tablets (28) using a tablet compression press (e.g., a Stokes 328 Press) and finally coated (30). The time between completion of the blending process and the tablet compression step (28) must be no more than 24 hours (e.g., within 24 hours).

In another embodiment the invention provides a method of making a tablet that comprises 320 mg. of saw palmetto, about 75 IU of d-alpha tocopherol, about 12.5 mg. of d-gamma tocopherol, about 4.5 mg. of mixed tocopherols including both d-beta tocopherol and d-delta tocopherol, about 100 mcg of selenium, about 2.5 mg. of lycopene complex, about 7.5 mg. of zinc, about 1 mg. of folic acid, about 250 mg. of vitamin $B_{12}$ and about 12.5 mg. of vitamin $B_6$, comprising: (a) forming a first admixture that comprises saw palmetto (b) forming a second admixture that comprises d-gamma and/or mixed tocopherols; (c) combining said first and second admixtures to form a third admixture; and (d) compressing or molding said third admixture into a tablet; wherein said first and/or second admixture further comprises zinc, selenium, or a mixture thereof.

In still another embodiment that draws from the unexpected benefits from forming the tablet within 24 hours of admixture formation, the invention provides a method of making a tablet comprising: (a) forming an admixture comprising (i) about 320 mg. of saw palmetto, about 75 IU of d-alpha tocopherol, about 12.5 mg. of d-gamma tocopherol, about 4.5 mg. of mixed tocopherols including both d-beta tocopherol and d-delta tocopherol, about 100 mcg of selenium, about 2.5 mg. of lycopene complex, about 7.5 mg. of zinc, about 1 mg. of folic acid, about 250 mg. of vitamin $B_{12}$ and about 12.5 mg. of vitamin $B_6$; or (ii) about 150 IU of d-alpha tocopherol, about 25 mg. of d-gamma tocopherol, about 9 mg. of mixed tocopherols including both d-beta tocopherol and d-delta tocopherol, about 200 mcg. of selenium, about 5 mg. of lycopene complex, about 15 mg. of zinc, about 2 mg. of folic acid, about 500 mcg. of vitamin $B_{12}$ and about 25 mg. of vitamin $B_6$, and (b) compressing or molding said admixture into a tablet within about 24 hours of step (a). The method is preferably performed during 5, 10, 20 or more sequential batches without any batches that exceed the 24 hour deadline.

III. Formulations and Administration

Preferably, the compositions of the present invention are prepared in a tablet dosage form, and most preferably a medium oval tablet. However it will be understood by those skilled in the art that other dosage forms may also be suitably prepared by known methods, for example, capsules, powders, pastes, liquids and similar oral dosage forms. Solid dosage forms of the present invention may be created using any pharmaceutically acceptable excipients such as fillers or extenders, binders, humectants, disintegrating agents, wetting agents, flavoring agents, coloring agents, and lubricants. Suitable pharmaceutically acceptable excipients are described in "Remington: The Science and Practice of Pharmacy," Lippincott Williams & Wilkins, Baltimore, Md. (2000), incorporated herein by reference.

The resulting formulation has a surprisingly low weight and size based upon that weight, and is preferably present as an oval tablet (preferably a medium oval tablet) having the following dimensions and weights:

Formulations without Saw Palmetto

Weight—from about 1500 to about 1,650 mg., from about 1525 to about 1625 mg., or about 1575 mg.

Length—from about 0.850 to about 0.900 inches, or about 0.875 inches

Width—from about 0.350 to about 0.400 inches, or about 0.375 inches

Thickness—from about 0.250 to about 0.325 inches, from about 0.280 to about 0.300 inches, or about 0.290 inches.

Formulations with Saw Palmetto

Weight—from about 1,550 to about 1,750 mg., from about 1,600 to about 1,700 mg., or about 1,650 mg.

Length—from about 0.850 to about 0.900 inches, or about 0.875 inches

Width—from about 0.350 to about 0.400 inches, or about 0.375 inches

Thickness—from about 0.0.275 to about 0.335 inches, from about 0.295 to about 0.315 inches, or about 0.305 inches.

It will be understood that an otherwise rounded tablet of equivalent volume could also be manufactured using the methods of the present invention.

The oval tablet form was selected because of the ease with which it can be swallowed and its compact dimensions relative to its overall volume. It will be recognized by workers of skill in the art that the foregoing dimensions are not absolute, and that the shape and dimensions of the oval tablet can be varied and still provide a tablet that is easily swallowed. It will also be recognized that these weights and dimensions vary from tablet to tablet due to manufacturing and batch-to-batch variability. The term "about" accommodates such immaterial changes to the overall weight, shape and dimensions of the tablet.

The compositions of the present invention are also preferably formulated so that they are extended release compositions, as defined in the US Pharmacopeia/National Formulary, section 711 [USP 25, United States Pharmacopeial Convention, Inc., 2002]. As suggested therein, the compositions should have an extended release profile in accordance with the specification related to extended release solid dose formulations. Additionally, the dissolution profiles of the compositions of the present invention preferably have a similarity factor ($f_2$) value between about 50 and about 100, as defined by the following equation:

$$f_2 = 50 \text{LOG} \left\{ \left[ 1 + 1/n \sum_{t=1}^{n} (R_t - T_t)^2 \right]^{-0.5} \times 100 \right\}$$

wherein $R_t$ and $T_t$ are the percent of composition dissolved at each time point.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

The formulations of the present invention are suitably administered once, twice, thrice or four times daily, though preferably are administered just once daily.

EXAMPLES

Example 1

Formulation Containing Natural Vitamin E

A first group of ingredients (Group 1), consisting of 44.625 kg of Vitamin E succinate, 34.8 kg of natural mixed tocopherol, 42.975 kg of chelated selenium (0.2%), 41.4 kg of zinc gluconate (12%), 30.0 kg of cellulose, 0.450 kg of magnesium stearate, 1.2 kg of silica (Sipernat 50 "Degussa"), 65.349 kg of microcrystalline cellulose and 6.531 kg of starch (Starch 1500) are weighed out. A second group of ingredients (Group 2), consisting of 1.5 kg of lycopene complex (5%), 6.00 kg of folic acid (10-12%), 18.750 kg of vitamin $B_{12}$, 11.430 kg of vitamin $B_6$, 3.0 kg. of PVP (Plasdone) K30, and 151.5 kg of dicalcium phosphate (Di-Cafos; 23% CA) are weighed out. Additional silica (9.45 kg) and magnesium stearate, vegetable grade (3.540 kg), which function as flow agents/oil absorbers and surface lubricants, respectively, are weighed out separately.

The Group 1 ingredients, including active ingredients, minerals, and formulators, are pre-blended in order to dilute the vitamins, especially the high oil-containing vitamins, and allow oscillation to occur. The ingredients are blended and oscillated for a time period sufficient to standardize the particle sizes of the materials.

Separately, a pre-blend is performed, mixing all the ingredients in Group 2 so as to dilute the vitamins with dicalcium phosphate. Following blending, the materials are oscillated so as to standardize the particle sizes of the raw materials.

The Group 1 blend of materials are subjected to a chilsonation (dry granulation) process, creating granules of a size sufficient to allow compression of the materials into tablet or capsule form. This step of the process also serves to further dilute oils from the Vitamin E materials into the minerals.

A final blending of the Group 1 and Group 2 materials is accomplished by loading the Group 1 and Group 2 mixtures into a Twin Shell Blender (Patterson Industries, Ltd, Cleveland, Ohio, USA) and mixing them together for approximately 8 minutes. The additional silica and magnesium stearate mixture is then added to the mixture and the entire contents of the blender mixed together for a time of approximately 2 minutes.

The final composition blend, now in the form of a flowing powder, is removed from the blender and placed into a tableting press such as the Korsch Pharmapress 230, 250, and 350 presses (Korsch Tableting, Somerville, N.J.), the Manesty D3B press, or the Stokes 328 presses, having adequate capacity and showing the exact pressures and precompression needed to maintain a stable and uniform ZIA. Here, the mixture is compressed into tablets, and the tablets are then coated using standard techniques, such as continuous coating, autokinetic coating, or pan coating.

Example 2

Formulation Containing Natural Vitamin E and Saw Palmetto

The ingredients of the final composition are weighed out into specific groups. The first group, Group 1, consists of 96 kg of saw palmetto (in the form of berry extract, 45%), 20.7 kg of zinc gluconate, 12%, 70.125 kg of dicalcium phosphate (DiCafos, 23% CA; Gallard-Schlesinger Ind., Plainview, N.Y.), 37.5 kg of microcrystalline cellulose, 7.5 kg of starch (Starch 1500®, Colorcon, Chalfont, Pa.), 1.8 kg of silica (Sipernat 50 "Degussa", Jefo Nutrition Inc., St-Hyacinthe, Quebec, Canada), and 0.90 kg of magnesium stearate-Vegetable Grade. The second group of ingredients (Group 2) consists of 26.033 kg of Vitamin E succinate (1210 IU), 17.4 kg of natural vitamin E mixed tocopherols, 27.892 kg of cellulose, 0.750 kg of silica (Sipernat 50 "Degussa", Jefo Nutrition Inc., St-Hyacinthe, Quebec, Canada), 0.360 kg of magnesium stearate-Vegetable grade, 21.510 kg of chelated selenium (0.2%), 0.750 kg of lycopene complex (5%), 3.00 kg of folic acid (10-12%), 9.375 kg of vitamin $B_{12}$ (1% Trit on DCP (dicalcium phosphate)), 5.730 kg of Vitamin $B_6$ (pyridoxine HCl, 82%), 3.30 kg of polyvinylpyrrolidone K30 (PVP K30), 70.650 kg of dicalcium phosphate (DiCafos, 23% CA; Gallard-Schlesinger Ind., Plainview, N.Y.), and 37.5 kg of microcrystalline cellulose.

A third group of ingredients, Group 3, includes microcrystalline Cellulose (14.850 kg), and silica (3.650 kg), which are weighed out and set aside.

The Group 1 compounds are blended together in a 30 ft³ Twin Shell Blender for a period of time of approximately 8 minutes, unloaded from the blender, and then oscillated using a Stokes Oscillator with a #0012 mesh screen into clean poly-lined barrels. Similarly, the Group 2 compounds are blended together in a Twin Shell Blender and oscillated using a Stokes Oscillator fitted with a #0012 mesh screen. The Group 1 and Group 2 mixtures are then each taken through a Chilsonation process separately, using a Vector Roller Compactor, creating a standardized particle size for use in tablet compression.

The Group 1 mixture is then blended with 9.0 kg of silica (Sipernat 50) and 4.0 kg of magnesium stearate—Vegetable Grade in a 30 ft³ Twin Shell Blender for approximately 8 minutes. The Group 2 items and the Group 3 items are then added to the mixture and the entire composition blended for approximately 8 minutes. Additional magnesium stearate—Vegetable Grade (4.725 kg) is then added, and the entire mixture blended for a further 2 minutes. The final composition blend is then loaded into clean, poly-lined barrels.

The final composition blend, now in the form of a flowing powder, is removed from the blender and placed into a tableting press such as the Korsch Pharmapress 230, 250, and 350 presses (Korsch Tableting, Somerville, N.J.), the Manesty D3B press, or the Stokes 328 presses, having adequate capacity and showing the exact pressures and precompression needed to maintain a stable and uniform ZIA. Here, the mixture is compressed into tablets, and the tablets are then coated using standard techniques, such as continuous coating, autokinetic coating, or pan coating.

Example 3

Failed Blending Attempt

Saw palmetto, vitamin E succinate, natural Vitamin E, zinc gluconate, cellulose, polyvinylpyrrolidone, magnesium stearate, and silica were weighed out and set aside as the Group 1 mixture.

Chelated selenium, lycopene complex, folic acid, zinc gluconate, vitamin B12, vitamin B6, dicalcium phosphate microcrystalline cellulose, and starch were all weighed out and set aside as the Group 2 mixture.

Both the Group 1 and the Group 2 mixture were separately blended and oscillated using a Stokes Oscillator with a mesh screen. Group 1 and Group 2 were then blended together in a Twin Shell Blender for approximately 5 minutes. Silica was added, and the mixture blended together for an additional 8 minutes. Finally, magnesium stearate was added and the mixture blended for an additional 2 minutes.

Attempts at chilsonation and tablet compression failed due to excessive stickiness of the composition.

Example 4

A tablet was prepared according to the process described in Example 1. The final product was a white, film-coated tablet having a specific shape suitable for oral administration and containing the following active ingredients, and amounts (amounts given in amount/tablet):

TABLE 1

| Ingredient | Amount | |
|---|---|---|
| Vitamin E (as d-alpha tocopheryl succinate) | 150 | IU |
| Vitamin E (as d-gamma tocopherol) | 25 | mg |
| Vitamin E (as d-delta, d-beta tocopherol) | 9 | mg |
| Selenium | 200 | mcg (0.2 mg) (based upon elemental selenium) |
| Lycopene complex | 5 | mg (based upon the weight of the complex |
| Zinc | 15 | mg (based on elemental zinc) |
| Folic acid | 2 | mg |
| Vitamin $B_{12}$ (cyanocobalamin) | 500 | mcg (0.5 mg) |
| Vitamin $B_6$ (pyridoxine HCl) | 25 | mg (based on weight of base) |

The tablets each also contained dicalcium phosphate, microcrystalline cellulose, maltodextrin, cellulose, soy protein, silica, modified corn starch, magnesium stearate, polyvinylpyrrolidone, titanium dioxide, polydextrose, hydroxypropyl methylcellulose, triacetin, and polyethylene glycol.

Example 5

A tablet was prepared according to the process described in Example 2. The final product was a white, film-coated tablet having a specific shape suitable for oral administration and containing the following active ingredients, and amounts (amounts given in amount/tablet):

TABLE 2

| Ingredient | Amount |
|---|---|
| Saw Palmetto | 320 mg |
| Vitamin E (as d-alpha tocopheryl succinate) | 75 IU |
| Vitamin E (as d-gamma tocopherol) | 12.5 mg |
| Vitamin E (as d-delta, d-beta tocopherol) | 4.5 mg |
| Selenium | 100 mcg (0.1 mg) |
| Lycopene complex | 2.5 mg |
| Zinc | 7.5 mg |
| Folic acid | 1 mg |
| Vitamin $B_{12}$ (cyanocobalamin) | 250 mcg (0.250 mg) |
| Vitamin $B_6$ (pyridoxine HCl) | 12.5 mg |

The tablets each also contain dicalcium phosphate, microcrystalline cellulose, maltodextrin, cellulose, soy protein, silica, modified corn starch, magnesium stearate, polyvinylpyrrolidone, titanium dioxide, polydextrose, hydroxypropyl methylcellulose, triacetin, and polyethylene glycol.

Example 6

Formulations were prepared in order to compare the effect of varying the weight ratios of zinc to natural tocopherols and selenium to natural tocopherols on the processing of the formulation into tableted form. In addition to the formulations reported in examples 4 and 5, the following formulations were prepared:

Comparative Formulation 1

300 I.U. of d-alpha tocopheryl succinate, 50 mg of d-gamma tocopherol, 13 mg of mixed tocopherols including d-delta tocopherol and d-beta tocopherol, 200 mcg of selenium chelate, 5 mg of lycopene complex, 15 mg of zinc gluconate, 2 mg of folic acid, 500 mcg of cyanocobalamin, 25 mg of pyridoxine HCL.

Comparative Formulation 2

320 mg saw palmetto extract, yielding 144 mg of fatty acids and sterols, 150 I.U. of d-alpha tocopheryl succinate, 25 mg of d-gamma tocopherol, 6.5 mg of mixed tocopherols including d-delta tocopherol and d-beta tocopherol, 100 mcg of selenium chelate, 2.5 mg of lycopene complex, 7.5 mg of zinc gluconate, 1 mg of folic acid, 250 mcg of cyanocobalamin, 12.5 mg of pyridoxine HCL.

Other ingredients in the comparative formulations included dicalcium phosphate; cellulose; maltodextrin; microcrystalline cellulose; modified corn starch; soy protein, enzymes, sodium selenite and citric acid contained within the selenium chelate; silica; sucrose and corn starch contained in the lycopene complex; polyvinylpyrrolidone; magnesium stearate; and titanium dioxide, polydextrose, hydroxypropyl methylcellulose, triacetin and polyethylene glycol as coating ingredients.

Comparative Formulations 1 and 2 exhibited poor processability during the tableting process.

TABLE 3

| | Zn/natural tocopherols (wt/wt) | Se/natural tocopherols (wt/wt) |
| --- | --- | --- |
| Example 1 | 0.44 | 0.0059 |
| Example 2 | 0.44 | 0.0059 |
| Comparative Formulation 1 | 0.24 | 0.0032 |
| Comparative Formulation 2 | 0.24 | 0.0032 |

All of the compositions, methods, and/or processes disclosed and claimed herein can be made and executed without undue experimentation in light of the present disclosure. While the compositions and methods of this invention have been described in terms of preferred embodiments, it will be apparent to those of skill in the art that variations may be applied to the compositions, methods and/or processes and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

What is claimed is:

1. A method of making a tablet comprising d-gamma, d-beta, and d-delta tocopherols (hereafter "tocopherols") comprising: a) combining said tocopherols with a zinc component and a selenium component and optionally saw palmetto in a zinc:tocopherol weight ratio of greater than or equal to about 0.44 and a selenium:tocopherol weight ratio of greater than or equal to about 0.0059, based on the elemental weights of zinc, selenium and tocopherols, to form a combination, and b) compressing or molding said combination into a tablet, wherein, when present, said saw palmetto is present in a saw palmetto:tocopherol weight ratio of about 18.8.

2. The method of claim 1 wherein said zinc component comprises zinc gluconate.

3. The method of claim 1, wherein said selenium component comprises chelated selenium.

4. The method of claim 1 wherein said tablet comprises from about 5 to about 50 mg. of d-gamma tocopherols and from about 1.5 to about 25 mg. of d-beta and d-delta tocopherols combined.

5. The method of claim 1 wherein said tablet comprises from about 10 to about 50 mg. of d-gamma tocopherols and from about 2 to about 20 mg. of d-beta and d-delta tocopherols combined.

6. The method of claim 1 wherein said tablet comprises from about 5 to about 50 mg. of d-gamma tocopherols and from about 1.5 to about 25 mg. of d-beta and d-delta tocopherols combined, said zinc component comprises zinc gluconate, and said selenium component comprises chelated selenium.

7. The method of claim 1 wherein said tablet comprises from about 10 to about 50 mg. of d-gamma tocopherols and from about 2 to about 20 mg. of d-beta and d-delta tocopherols combined, said zinc component comprises zinc gluconate, and said selenium component comprises chelated selenium.

8. A molded or compressed tablet comprising:
a) a mixture of oleophllic tocopherols comprising d-gamma, d-beta, and d-delta tocopherols (hereafter "tocopherols");
b) a zinc component and a selenium component in a zinc:tocopherol weight ratio of greater than or equal to about 0.44 and a selenium:tocopherol weight ratio of greater than or equal to about 0.0059, based on the weight of elemental zinc, selenium, and tocopherols;
c) optionally saw palmetto in a saw palmetto:tocopherol weight ratio of about 18.8.

9. The tablet of claim 8 wherein said zinc component comprises zinc gluconate.

10. The tablet of claim 8 wherein said selenium component comprises chelated selenium.

11. The tablet of claim 8 wherein said tablet comprises from about 5 to about 50 mg. of d-gamma tocopherols and from about 1.5 to about 25 mg. of d-beta and d-delta tocopherols combined.

12. The tablet of claim 8 wherein said tablet comprises from about 10 to about 50 mg. of d-gamma tocopherols and from about 2 to about 20 mg. of d-beta and d-delta tocopherols combined.

13. The tablet of claim 8 wherein said tablet comprises from about 5 to about 50 mg. of d-gamma tocopherols and from about 1.5 to about 25 mg. of d-beta and d-delta tocopherols combined, said zinc component comprises zinc gluconate, and said selenium component comprises chelated selenium.

14. The tablet of claim 8 wherein said tablet comprises from about 10 to about 50 mg. of d-gamma tocopherols and from about 2 to about 20 mg. of d-beta and d-delta tocopherols combined, said zinc component comprises zinc gluconate, and said selenium component comprises chelated selenium.

15. A tablet comprising:
a) a mixture of oleophilic tocopherols comprising d-gamma, d-beta, and d-delta tocopherols (hereafter "tocopherols");
b) a zinc component and a selenium component in an amount sufficient to stabilize said oleophilic tocopherols in said tablet, having a zinc:tocopherol weight ratio of greater than or equal to about 0.44 and a selenium:tocopherol weight ratio of greater than or equal to about 0.0059, based on the weight of elemental zinc, selenium, and tocopherols;
c) optionally saw palmetto in a saw palmetto:tocopherol weight ratio of about 18.8.

16. The tablet of claim 15 wherein said zinc component comprises zinc gluconate.

17. The tablet of claim 15 wherein said selenium component comprises chelated selenium.

18. The tablet of claim 15 wherein said tablet comprises from about 5 to about 50 mg. of d-gamma tocopherols and from about 1.5 to about 25 mg. of d-beta and d-delta tocopherols combined.

19. The tablet of claim 15 wherein said tablet comprises from about 10 to about 50 mg. of d-gamma tocopherols and from about 2 to about 20 mg. of d-beta and d-delta tocopherols combined.

20. The tablet of claim 15 wherein said tablet comprises from about 5 to about 50 mg. of d-gamma tocopherols and from about 1.5 to about 25 mg. of d-beta and d-delta tocopherols combined, said zinc component comprises zinc gluconate, and said selenium component comprises chelated selenium.

* * * * *